United States Patent
Gregorio Gracia

[11] Patent Number: 5,154,610
[45] Date of Patent: Oct. 13, 1992

[54] POSITIONING STUD FOR MASTER MODELS

[75] Inventor: Oscar R. Gregorio Gracia, Leganes, Spain

[73] Assignee: Getri Instrumental S.A., Madrid, Spain

[21] Appl. No.: 432,065

[22] Filed: Nov. 6, 1989

[51] Int. Cl.$^5$ .............. A61C 5/08; A61C 19/00; F16B 35/00

[52] U.S. Cl. .................. 433/74; 433/221; 411/388; 411/403

[58] Field of Search .......... 411/388, 400, 401, 402, 411/403; 433/74, 221, 225

[56] References Cited

U.S. PATENT DOCUMENTS

| | | | |
|---|---|---|---|
| 2,087,881 | 7/1937 | Bastagle | 411/403 |
| 2,155,498 | 4/1939 | Laudensack | 411/403 |
| 3,031,049 | 4/1962 | Somville | 411/403 |
| 4,085,650 | 4/1978 | Flynn | 411/403 |
| 4,363,625 | 12/1982 | der Avanessian | 433/74 |
| 4,371,340 | 2/1983 | Imaizumi | 433/74 |
| 4,443,192 | 4/1984 | Blitz | 433/74 |
| 4,521,188 | 6/1985 | Metzler | 433/74 |

FOREIGN PATENT DOCUMENTS

| | | | |
|---|---|---|---|
| 931415 | 10/1947 | France | 411/388 |
| 1233576 | 5/1960 | France | 411/388 |
| 46-33047 | 8/1967 | Japan | 411/403 |

*Primary Examiner*—Neill R. Wilson
*Attorney, Agent, or Firm*—Darby & Darby

[57] ABSTRACT

A positioning stud for master models, formed by a cylindrical body, in which approximately one third of its length is threaded, this threaded area being separated from the rest which is smooth, by a circular boss, to limit the threaded area being inserted in the master model concerned. The free end of the stud is adequately shaped to fit the auxiliary tool used to place it in the model.

8 Claims, 1 Drawing Sheet

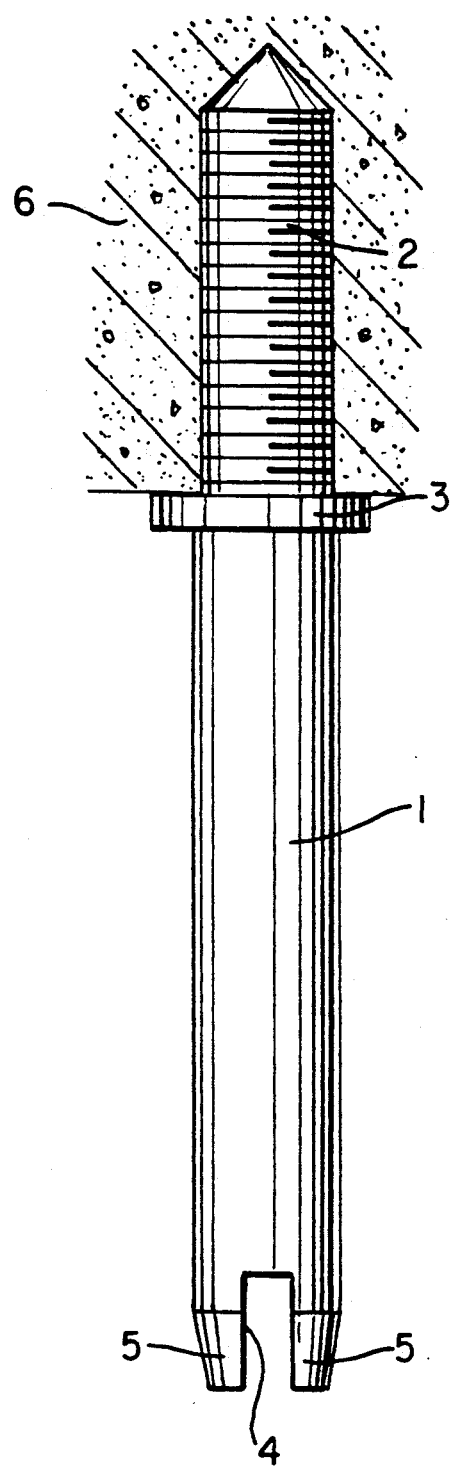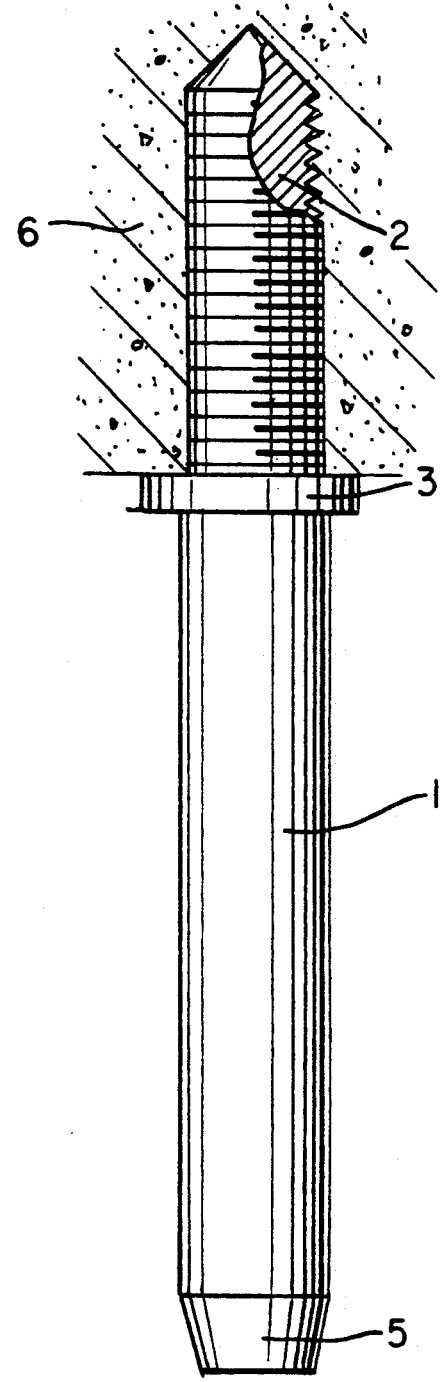

POSITIONING STUD FOR MASTER MODELS

BACKGROUND OF THE INVENTION

The present invention relates to positioning studs for master models for dental prostheses and the like.

Conventionally, positioning studs which are used are simple smooth shanks. The shanks are adapted and placed in holes, which correspond to the model, by using an adhesive or glue. This requires that the adhesive be very fast-drying to ensure that the adhesive secures completely and quickly and that great care be taken when placing the positioning studs in the holes so that they do not slant. This implies a combination of special care, speed and accuracy, which are difficult to combine. Therefore, there will always be disadvantages in using smooth shanks, which are normally utilized.

SUMMARY OF THE INVENTION

The present invention is directed to an easy-to-place positioning stud which is accurate and overcomes the difficulties in using conventional positioning studs. The stud has a threaded area, limited from the rest of the stud by a small boss. The stud is intended to be inserted mechanically into a hole previously made in the model and does not need any type of glue. The stud is perfectly secured and leaves the rest of the stud, which is a smooth shank, to remain in its proper place. The end of the shank is shaped like a tongue or groove to assist with the screwing of the shank by a respectively auxiliary tool, which is applied to the tongue or groove.

BRIEF DESCRIPTION OF THE DRAWINGS

The positioning stud for master models of the present invention will be described in detail, with reference to the attached drawing which shows a preferred form of embodiment of the invention. The preferred form is simply by way of example and is not limiting, but is subject to any variations in detail which do not involve a fundamental alteration of its essential features.

FIG. 1 is an elevational plan view of a stud with a groove at the free end of the stud.

FIG. 2 is an elevational plan view of between projected areas taken from the left or right of FIG. 1.

DESCRIPTION OF THE PREFERRED EMBODIMENT

FIGS. 1 and 2 show a positioning stud for master models that comprises a cylindrical body with a suitable diameter. About one third of the length of the body 1 is provided with a threaded area 2, which is specifically designed for each particular application. A boss 3 separates the threaded area 2 from the smooth area 1. The boss has a slightly larger diameter than the stud so that it forms a stop when inserted. The end of the smooth area 1 forms a diametrical groove 4 (FIG. 1) 5 (FIG. 2) or any other shape, such as a star, for example, where the suitable auxiliary screwing tool fits.

The stud made in this way is placed in the base of a plaster positive, in which holes have previously been made. The holes have a suitable diameter for enabling the threaded area 2 to be inserted in them by means of the screw pitch of the threaded area. In this manner, the plaster positive is perfectly secured to the stud by a screw threaded system without the presence of any type of glue whatsoever.

After the studs 1 have been placed in the plaster positive, the respective parts corresponding to the model concerned in each case are fitted on the smooth area 1. Advantages of the invention include eliminating the need for glues, ensuring a perfectly secure fit by screwing, and enabling the possibility of removing the studs by unscrewing when required for use elsewhere. Conventional studs at present cannot be re-used, because they are secured by glues and their point of application cannot be corrected once in place.

The shape, materials and dimensions may be varied and accessories added provided this does not alter, change or modify the essential nature of the present invention.

I claim:

1. A combination useful for positioning in master models, comprising:

a positioning stud having a body with a smooth portion and a threaded portion, said threaded portion being threaded with a screw pitch, the smooth portion having a free end distal from the threaded portion;

a plaster positive into which is inserted said threaded portion, said plaster positive threadably engaging said threaded portion to enable screwing and unscrewing of the stud in the plaster positive;

stop means for limiting insertion of said positioning stud into said plaster positive, said stop means including a boss which has a diameter that is larger than that of said threaded portion, said boss being located between said threaded and smooth portions; and engaging means adapted for cooperative engagement by a tool for screwing the positioning stud into the plaster positive, said engaging means being at the free end of the smooth portion.

2. A combination as in claim 1, wherein said threaded portion has a length which is approximately one-third the length of said positioning stud.

3. A combination as in claim 1, wherein said free end has a groove.

4. A combination as in claim 1, wherein said free end has two projections.

5. A combination as in claim 1, wherein said body is cylindrical and said boss is circular.

6. In combination, a master plasterer model for a dental prothesis having a hole therein for reception of a positioning stud, and a positioning stud having a smooth portion and a threaded portion, said threaded portion being threaded with a screw pitch and threadably positioned in the hole in said master plastic model to enable screwing and unscrewing of said stud in said master model, said positioning stud further comprising stop means for limiting insertion of said stud in said master plaster model, said stop means including a boss which has a diameter that is larger than that of said threaded portion, said boss being located between said threaded portion and said smooth portion, and said positioning stud further comprising means at the free end of said smooth portion adapted to receive a tool for screwing and unscrewing said positioning stud in said water plaster model.

7. A method useful for positioning in master models, comprising the steps of:

inserting a threaded portion of a body of a positioning stud into a plaster positive by threadably engaging the threaded portion with the plaster positive so as to enable screwing and unscrewing of the stud in the plaster positive;

screwing in the positioning stud with a tool engaged with a free end of the body, the free end being adapted for cooperative engagement by the tool; and limiting the insertion of the positioning stud with a boss that has a diameter which is larger in size than that of the threaded portion, the boss being between the threaded portion and smooth portion of the body.

8. A method as in claim 7, wherein the threaded portion has a length which is approximately one-third the length of the positioning stud.

* * * * *